(12) United States Patent
Lotter et al.

(10) Patent No.: US 8,802,400 B2
(45) Date of Patent: Aug. 12, 2014

(54) L-LYSINE-CONTAINING FEED ADDITIVES

(75) Inventors: Hermann Lotter, Altenstadt (DE);
Ulrich Becker, Freigericht-Horbach (DE); Frank Dübner, Friedberg (DE);
Friederike Kaeppke, Gelnhausen (DE);
Joachim Pohlisch, Gelnhausen (DE);
Ralf Kelle, Gütersloh (DE); Cory M. Sander, Omaha, NE (US); Lawrence Edward Fosdick, Oskaloosa, IA (US)

(73) Assignee: Evonik Degussa GmbH, Hanau (DE)

( * ) Notice: Subject to any disclaimer, the term of this patent is extended or adjusted under 35 U.S.C. 154(b) by 102 days.

(21) Appl. No.: 12/795,301

(22) Filed: Jun. 7, 2010

(65) Prior Publication Data
US 2010/0310714 A1  Dec. 9, 2010

Related U.S. Application Data

(62) Division of application No. 11/374,661, filed on Mar. 13, 2006, now abandoned.

(30) Foreign Application Priority Data

Oct. 8, 2005 (DE) .......................... 10 2005 048 315

(51) Int. Cl.
*C12P 13/08* (2006.01)
(52) U.S. Cl.
CPC ...................................... C12P 13/08 (2013.01)
USPC ........................................................ 435/115
(58) Field of Classification Search
CPC ....................................................... C12P 13/08
USPC ........................................................ 435/115
See application file for complete search history.

(56) References Cited

U.S. PATENT DOCUMENTS

| | | | |
|---|---|---|---|
| 5,133,976 A | 7/1992 | Rouy | |
| 5,275,940 A | 1/1994 | Kino et al. | |
| 5,431,933 A | 7/1995 | Binder et al. | |
| 5,622,710 A | 4/1997 | Binder et al. | |
| 5,770,409 A | 6/1998 | Pfefferle et al. | |
| 5,840,358 A | 11/1998 | Hofler et al. | |
| 5,840,551 A | 11/1998 | Werning et al. | |
| 5,876,780 A | 3/1999 | Virtanen et al. | |
| 5,990,350 A | 11/1999 | Stevens et al. | |
| 2003/0152633 A1 | 8/2003 | Kushiki et al. | |
| 2004/0115304 A1 | 6/2004 | Dubner et al. | |
| 2006/0117401 A1 * | 6/2006 | Schmitz et al. ............... 800/278 |

FOREIGN PATENT DOCUMENTS

| | | |
|---|---|---|
| DE | 1 056 082 | 4/1959 |
| DE | 2 006 555 | 6/1983 |
| DE | 4 100 920 A1 | 7/1992 |
| EP | 0 467 401 A1 | 1/1992 |
| EP | 0 533 039 A1 | 3/1993 |
| EP | 0 615 693 A2 | 9/1994 |
| EP | 0 743 016 A1 | 11/1996 |
| EP | 0 809 940 A2 | 12/1997 |
| EP | 0 923 878 A2 | 6/1999 |
| EP | 1 062 877 A1 | 12/2000 |
| EP | 1 067 192 A1 | 1/2001 |
| EP | 1 331 220 A2 | 7/2003 |
| EP | 1 582 101 B1 | 10/2005 |
| GB | 1 439 121 | 6/1976 |
| GB | 1 439 728 | 6/1976 |
| SU | 1386144 A1 | 4/1988 |
| SU | 1509018 A1 | 9/1989 |
| WO | WO 2004/005438 A1 | 7/2004 |
| WO | WO2004057003 A1 * | 7/2004 |
| WO | WO 2005/006875 A2 | 1/2005 |
| WO | WO 2005/021772 A1 | 3/2005 |

* cited by examiner

*Primary Examiner* — Benjamin Packard
(74) *Attorney, Agent, or Firm* — Smith, Gambrell & Russell LLP

(57) ABSTRACT

The invention relates to relatively light and thermally stable granulated, fermentation-broth-based animal feed additives having a high content of L-lysine and to low-loss methods for their production from broths obtained by fermentation.

8 Claims, 1 Drawing Sheet

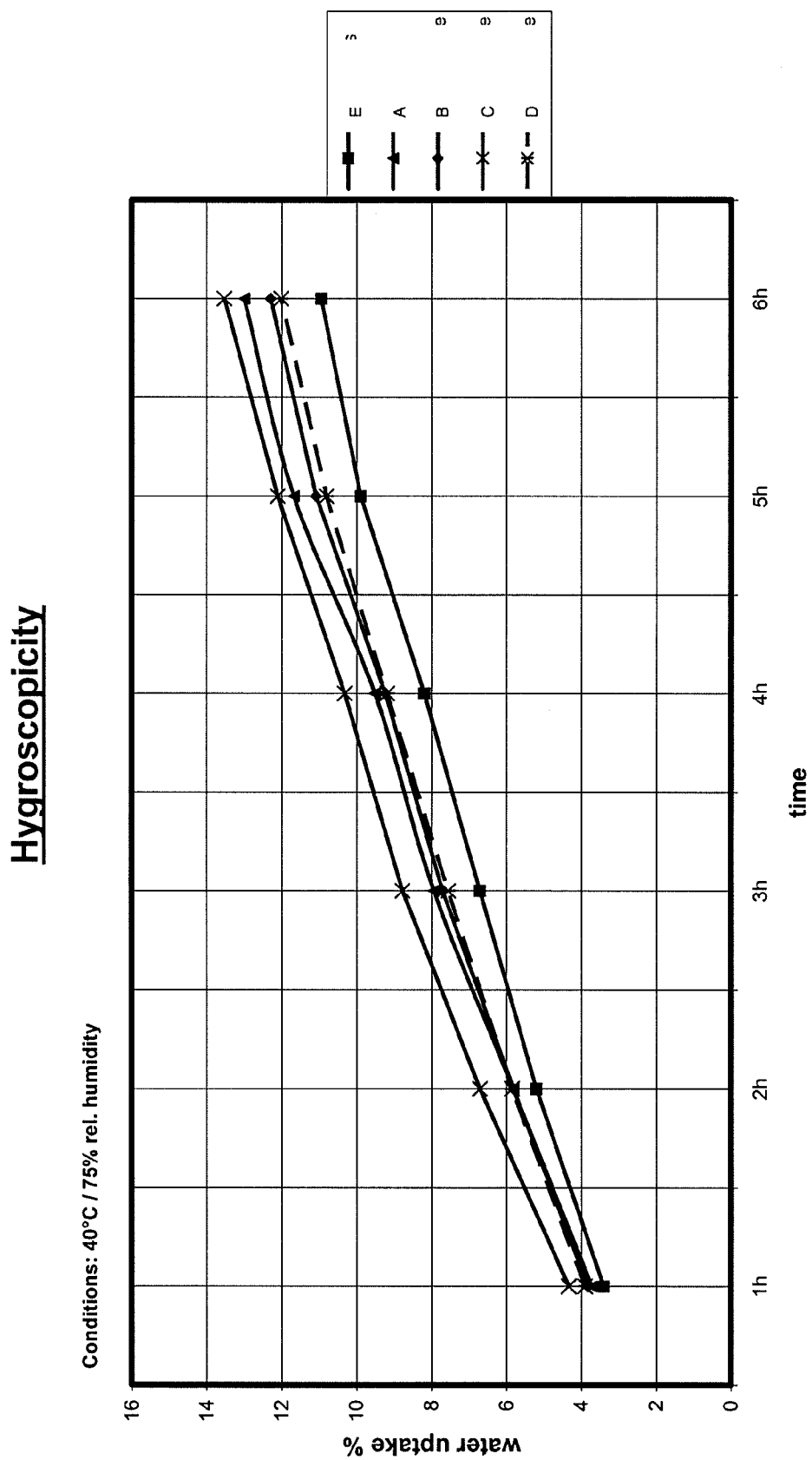

L-LYSINE-CONTAINING FEED ADDITIVES

REFERENCE TO RELATED APPLICATIONS

This application is a divisional of U.S. application Ser. No. 11/374,661, filed on Mar. 13, 2006 now abandoned which claims the benefit of German priority Application No. 10 2005 048 315.1 filed Oct. 8, 2005. Both documents are relied on and incorporated herein by reference.

BACKGROUND OF THE INVENTION

The invention relates to relatively light and thermally stable granulated, fermentation-broth-based animal feed additives having a high content of L-lysine and to low-loss methods for their production from broths obtained by fermentation.

PRIOR ART

Animal feeds are supplemented with individual amino acids in accordance with the requirements of the animals. For supplementation of animal feeds, e.g. with L-lysine, to date use is very predominantly made of L-lysine monohydrochloride having an L-lysine content of 78%. Since the L-lysine is produced by fermentation, it must, to produce the monohydrochloride, first be separated off from all other constituents of the crude fermentation broth in complex process steps, then converted into the monohydrochloride and the latter is crystallized. In the process a large number of byproducts and the reagents required for workup arise as waste. Since a high purity of the animal feed supplement is not always necessary, and in addition, in the fermentation byproducts, frequently nutritionally active valuable materials are still present, there has therefore been no lack of attempts in the past to avoid the complex production of feed amino acids, in particular pure L-lysine monohydrochloride, and to convert the crude fermentation broth more inexpensively into a solid animal feed.

The complex composition of such media has proved a serious disadvantage, since they can generally only be dried with difficulty, and are then hygroscopic, virtually not free-flowing, at risk of lump formation and unsuitable for the technically demanding processing in mixed feed works. This applies especially to L-lysine-containing fermentation products. Simple dewatering of the crude fermentation broth by spray drying led to a dusty, very hygroscopic concentrate which becomes lumpy after a short storage time, and in this form cannot be used as animal feed.

EP 0 533 039 relates to methods for producing an amino acid fermentation-broth-based animal feed supplement, the supplement being obtainable directly from the fermentation broth by spray drying. For this, in a variant, a part of the biomass is separated off upstream of the spray drying. By means of a very clean fermentation procedure, i.e. obtaining a fermentation broth which is low in residues of organic substances, the broth can be dried even without the biomass and without additional carrier to give handlable granules.

Solid concentrates containing approximately 20% by weight of L-lysine are disclosed by GB 1 439 121, in which L-lysine-containing fermentation broths having a pH of 4.5 and a bisulphite content are also described.

EP 0 615 693 discloses a method for producing a fermentation-broth-based animal feed additive in which the fermentation broth, if appropriate after removing part of the constituents, is spray-dried to produce a fine grain, at least 70% by weight of which has a maximum particle size of 100 μm, and this fine grain, in a second stage, is built up to produce granules containing the fine grain at least 30% by weight.

According to GB 1 439 728, an L-lysine-containing concentrate is produced from a fermentation broth which, upstream of the concentration, is acidified by HCl to a pH of approximately 6.4 and to which bisulphite is added for stabilization.

After concentration by evaporation, it is further acidified to a pH of 4.0, and the desired product obtained by spray drying.

EP-A 1 331 220 (≅US 2003/152633) relates to granulated feed additives which contain L-lysine as main component. There, it was found that the amount of the counterions for the lysine, such as, for example, that of the sulphate ions, can be decreased by using as counterion carbon dioxide formed in the fermentation. Overall, an anion/lysine ratio of 0.68 to 0.95 is claimed.

The reduction of the counterions, such as, e.g. sulphate, in the L-lysine-containing product is said to lead to an improvement of the hygroscopic properties and caking tendency.

OBJECT OF THE INVENTION

It is an object of the invention to provide an L-lysine-containing feed additive having improved properties which is produced using the broths arising in the fermentation, and a method having lower lysine loss during workup of the broths than known from the state of art.

DESCRIPTION OF THE INVENTION

The invention relates to a granulated fermentation-broth-based feed additive having a) an L-lysine content of 10 to 70% by weight (calculated as L-lysine base), in particular 30 to 60% by weight, b) a water content of 0.1 to 5% by weight of water, and a sulphate/L-lysine ratio of 0.85 to 1.2, preferably 0.9 to 1.0, in particular >0.9 to <0.95, this ratio being calculated according to the formula $V=2\times[SO_4^{2-}]/[L\text{-lysine}]$ this ratio being calculated from the formula $V=2\times[SO_4^{2-}]/[L\text{-lysine}]$.

The difference from 100% by weight is made up by the further constituents of the fermentation broth and if appropriate the biomass.

Preferably, the granules have a pH of 3.5 to 5.1, in particular 4.0 to 5.0, preferably 4.2 to 4.8, measured in a 10% strength by weight suspension in deionized water at 25° C. using a pH electrode. The measured value establishes itself at a constant value after approximately 1 min.

The molar ratio of sulphate to L-lysine is set subsequently to the fermentation, an $SO_4^{2-}$-containing compounds, in particular ammonium sulphate and sulphuric acid, being added in a suitable dilution.

"Fermentation-broth-based" means that an L-lysine-containing fermentation broth is worked up which contains the biomass formed during the fermentation at 0 to 100%.

The invention likewise relates to a method for producing a granulated L-lysine-containing feed additive by fermentation of an L-lysine-producing microorganism in an aqueous medium using ammonium sulphate and under aerobic conditions and producing a granulated product by intrinsically known methods, wherein, after completion of the fermentation optionally the ratio sulphate/L-lysine in the fermentation broth is measured.

The sulfate concentration in the fermentation broth is known. This is in general also true for the produced amounts of L-lysine. Said amounts are usually measured in the case of uncertainty.

BRIEF DESCRIPTION OF DRAWING

The accompanying drawing is a graph of hygroscopicity characteristics of product of the invention E compared to products A to D of the prior art.

DETAILED DESCRIPTION OF INVENTION

The process comprises the following steps:
a) Optionally subsequently ammonium sulphate is added and
b) the pH is lowered by adding sulphuric acid to 4.0 to 5.2, in particular 4.9 to 5.1, a sulphate/L-lysine ratio of 0.85 to 1.2, in particular 0.9 to 1.0, being set in the broth by the addition of the sulfate containing compound(s), and
c) the resultant mixture is preferably heated and concentrated by dehydration, granulated and a product is obtained which has an L-lysine content of 10 to 70% by weight (calculated as lysine base, based on the total amount) and a sulphate/L-lysine ratio of 0.85 to 1.2, in particular 0.9 to 1.0, in particular >0.9 to <0.95, the ratio being calculated from the formula $$2 \times [SO_4^{2-}]/[\text{L-lysine}] = V.$$

A ratio V=1 means, for example, that a stoichiometrically composed $(SO_4)Lys_2$ is present, whereas at a ratio of 0.9, a 10% sulphate deficit is found.

Step b) can also be carried out before step a).

Preferably the product has a L-Lysine content of 20 to 65, most preferably 30 to 65% by weight.

It is possible to carry out the fermentation in the presence of an amount of ammonium sulphate such that after completion of the fermentation a sulphate/lysine ratio is already present which is in the range claimed by the invention.

Further addition of ammonium sulphate may then no longer be necessary.

If acid is added beyond the inventive pH reduction, because of the buffering action of the compounds present in the broth, increased amounts of acid are necessary, which can then lead to unwanted denaturation and disintegration of the cells.

Even without addition of an acid, the pH of the broth during the concentration by evaporation falls to a pH of approximately 5.4.

The granules produced according to the invention have a pH of 3.5 to 5.1 (measured in the suspension, see above). The addition of hydrochloric acid is preferably excluded. Its portion is in general at max. 1%, preferably 0.01 to 0.1% by weight, related to the amount of sulphuric acid.

The granules, despite the increased sulphate content, have a markedly higher degree of whiteness, a lower hygroscopicity and a better stability under thermal stress than granules having the same L-lysine content, as are known from the prior art (see examples) which, in suspension, exhibit a pH of 5.3 to 5.7, and a sulphate/L-lysine ratio in the range of, for example, from 0.75 to 0.87.

The said properties may be further improved by adding sulphites in an amount of 0.01 to 0.5%, preferably 0.1 to 0.3, by weight, in particular 0.1 to 0.2% by weight, based on the fermentation broth.

Said sulphites, especially ammonium-, earthalkali or alkalisalts of sulphurous acid or mixtures thereof, in particular sodium hydrogensulphite, are preferably added as solution to the fermentation broth before concentration. The amount used is preferably taken into consideration during setting the sulfate/L-lysine ratio.

The granules may be produced, for example, by the methods according to EP-B 0 615 693 or EP-B 0 809 940, U.S. Pat. No. 5,840,358 or WO 2005/006875 or WO 2004/054381. Generally, >97% have a mean particle size of >0.1 to 1.8 mm, and a bulk density of 600 to 950 kg/m$^3$, in particular 650 to 900 kg/m$^3$.

The colour values of the granules are preferably in the ranges:
without hydrogensulphite addition: L*65-70, a*6-8, b*20-25
with hydrogensulphite addition: L*>70-80, a*4-<6, b*>25-30.

However, the inventive method does not only lead to products showing advantageous properties.

It is found, at the same time, that the lysine loss which generally occurs in the workup of fermentation broth can be lowered by approximately 50% by the acidification according to the invention and setting the sulphate/lysine ratio before concentration.

Fermentation of the coryneform bacteria preferably used according to the invention, in particular of the species *Corynebacterium glutamicum* can be carried out continuously, for example as described in PCT/EP 2004/008882, or discontinuously in the batch method, or in the fed batch method or repeated fed batch method for the purpose of producing L-lysine. A general summary on known cultivation methods is available in the textbook by Chmiel (Bioprozesstechnik 1. Einführung in die Bioverfahrenstechnik [Bioprocess technology 1. Introduction to bioengineering technology] (Gustav Fischer Verlag, Stuttgart, 1991)) or in the textbook by Storhas (Bioreaktoren and periphere Einrichtungen [Bioreactors and peripheral devices] (Vieweg Verlag, Brunswick/Wiesbaden, 1994)).

The culture medium and fermentation medium to be used must appropriately satisfy the requirements of the respective strains. Descriptions of culture media of various microorganisms are present in the handbook "Manual of Methods for General Bacteriology" of the American Society for Bacteriology (Washington D.C., USA, 1981). The terms culture medium and fermentation medium or medium are mutually exchangeable.

As carbon source, use can be made of sugars and carbohydrates, for example glucose, sucrose, lactose, fructose, maltose, molasses, sucrose-containing solutions from sugar beet or sugar cane production, starch, starch hydrolysate and cellulose, oils and fats, for example soya oil, sunflower oil, peanut oil and coconut fat, fatty acids, for example palmitic acid, stearic acid and linoleic acid, alcohols, for example glycerol, methanol and ethanol, and organic acids, for example acetic acid. These substances can be used individually or as a mixture.

As nitrogen source, use can be made of organic nitrogenous compounds such as peptones, yeast extract, meat extract, malt extract, maize steep liquor, soya bean meal and urea, or inorganic compounds such as ammonium sulphate, ammonium phosphate, ammonium carbonate and ammonium nitrate, preferably ammonium sulphate. The nitrogen sources can be used individually or as a mixture.

As phosphorus source, use can be made of phosphoric acid, potassium dihydrogenphosphate or dipotassium hydrogenphosphate or the corresponding sodium salts.

The culture medium must in addition contain salts which are necessary for growth, for example in the form of sulphates of metals, for example sodium, potassium, magnesium, calcium and iron, for example magnesium sulphate or iron sulphate. Finally, use can be made of essential growth substances such as amino acids, for example homoserine and vitamins, for example thiamin, biotin or pantothenic acid, in addition to the above-mentioned substances. In addition, suitable precursors of the respective amino acid can be added to the culture medium.

The said feed materials can be added to the culture in the form of a single batch, or fed in a suitable manner during the culturing.

For pH control of the culture, use is made of basic compounds, such as sodium hydroxide, potassium hydroxide, ammonia or ammonia water, or acidic compounds such as phosphoric acid or sulphuric acid. The pH is generally set to 6.0 to 9.0, preferably 6.5 to 8. To control foam development, use can be made of antifoams, for example polyglycol esters of fatty acids. To maintain the stability of plasmids, suitable selectively active substances, for example antibiotics, can be added to the medium. To maintain aerobic conditions, oxygen or oxygen-containing gas mixtures, for example air, are introduced into the culture. The use of liquids which are enriched with hydrogen peroxide is likewise possible. If appropriate the fermentation is run at superatmospheric pressure, for example at a pressure of 0.03 to 0.2 MPa. The temperature of the culture is usually 20° C. to 45° C., and preferably 25° C. to 40° C. In the case of batch methods, culturing is continued until a maximum of the desired amino acid has formed. This target is usually achieved within 10 hours to 160 hours. In the case of continuous methods, longer culturing times are possible.

Examples of suitable fermentation media are found, inter alia, in the patent documents U.S. Pat. No. 5,770,409, U.S. Pat. No. 5,840,551 and U.S. Pat. No. 5,990,350, or U.S. Pat. No. 5,275,940.

Methods for determining L-amino acids are known from the prior art. The analysis can, for example, be performed as described in Spackman et al. (Analytical Chemistry, 30, (1958), 1190) by anion-exchange chromatography with subsequent ninhydrin derivatization, or it can be performed by reverse phase HPLC, as described in Lindroth et al. (Analytical Chemistry (1979) 51: 1167-1174).

The invention accordingly relates to a method for producing an L-amino acid in which a) a coryneform bacterium is fermented in a suitable medium and b) the L-amino acid is enriched in the fermentation broth or in the cells of the isolated coryneform bacterium.

The fermentation broth produced in this manner is subsequently further processed to form a solid or liquid product.

A fermentation broth is taken to mean a fermentation medium in which a microorganism was cultured for a certain time and at a certain temperature. The fermentation medium and the medium used during the fermentation contains/contain all of the substances and components which ensure multiplication of the microorganism and formation of the desired amino acid.

At completion of the fermentation, the resultant fermentation broth accordingly contains a) the biomass of the microorganism resulting from multiplication of the microorganism cells, b) the L-lysine formed in the course of fermentation, c) the organic byproducts formed in the course of fermentation and d) the constituents of the fermentation medium/fermentation media used which were not consumed by the fermentation and of the feed materials, for example vitamins such as biotin, amino acids such as homoserine, or salts such as magnesium sulphate.

The organic byproducts include substances which may be produced in addition to L-lysine, and excreted, by the microorganisms used in the fermentation. These include L-amino acids which make up less than 30%, 20% or 10%, relative to the desired amino acid. In addition, these include organic acids which bear one to three carboxyl groups, for example acetic acid, lactic acid, citric acid, malic acid or fumaric acid. Finally, these also include sugars, for example trehalose.

Typical fermentation broths suitable for industrial purposes have an L-lysine content of 40 g/kg to 180 g/kg, or 50 g/kg to 150 g/kg. The biomass content (as dried biomass) is generally 20 to 50 g/kg.

In the case of methods for producing lysine, those methods are preferred in which products are obtained which contain constituents of the fermentation broth. These are used in particular as animal feed additives.

Depending on requirements, the biomass can be entirely or in part removed from the fermentation broth by separation methods, for example centrifugation, filtration, decantation or a combination thereof, or left completely in it. If appropriate, the biomass or the biomass-containing fermentation broth is inactivated during a suitable process step.

In one processing method, the biomass is completely or virtually completely removed, so that none (0%) or at most 30%, at most 20%, at most 10%, at most 5%, at most 1%, or at most 0.1%, of biomass remains in the product produced. In a preferred processing method, the biomass is not removed or removed only in minor amounts, so that all (100%) or more than 70%, 80%, 90%, 95%, 99% or 99.9% of biomass remains in the product produced.

Fermentation broths from which the biomass has been in part or entirely removed can be used for standardizing the product. Obviously, this also applies to the pure compounds L-lysine base and lysine sulphate.

According to the invention, before the concentration, the fermentation broth obtained after the fermentation is acidified by sulphuric acid and if appropriate admixed with ammonium sulphate. Finally, the broth can also be stabilized and brightened by adding preferably sodium hydrogensulphite or another salt, for example ammonium salt, alkali metal salt or alkaline earth metal salt of sulphurous acid.

If biomass is separated off, this is preferably performed before the inventive lowering of the pH and the addition of ammonium sulphate and sulphite salt.

If the biomass is separated off, if appropriate, organic or inorganic solids present in the fermentation broth are in part or entirely removed. The organic byproducts dissolved in the fermentation broth and the dissolved non-consumed constituents of the fermentation medium (feed materials) remain at least in part in the product (>0%), preferably at least 25%, particularly preferably at least 50%, and very particularly preferably at least 75%. If appropriate, these also remain entirely (100%) in the product, or virtually entirely, that is >95%, or >98%. In this sense, the term "fermentation broth base" means that a product contains at least a part of the constituents of the fermentation broth.

Subsequently, water is removed from the broth using known methods, for example using a rotary evaporator, thin-film evaporator, falling-film evaporator, by reverse osmosis or by nanofiltration, or the broth is thickened or concentrated. This concentrated fermentation broth can subsequently be worked up to form free-flowing products, in particular granules, by methods of freeze drying, spray drying, spray granulation or by other methods, for example in the circulating fluidized bed according to PCT/EP 2004/006655. If appropriate, from the resultant granules, a product having the desired particle size is isolated by sieving or dust separation.

It is likewise possible to obtain a finely divided powder from the fermentation broth directly, i.e. without previous concentration by spray drying or spray granulation.

The particle size determination can be carried out using methods of laser diffraction spectrometry. The corresponding methods are described in the textbook on "Teilchengrößenmessung in der Laborpraxis" [Particle size measurement in laboratory practice] by R. H. Müller and R. Schuhmann, Wissenschaftliche Verlagsgesellschaft Stuttgart (1996) or in the textbook "Introduction to Particle Technology" by M. Rhodes, Wiley & Sons (1998).

The free-flowing, finely divided powder can be converted in turn into a coarse-grained, free-flowing, storable and substantially dust-free product by suitable compacting or granulation methods.

"Free-flowing" is taken to mean powders which, of a series of glass outlet vessels having different-sized outlet orifices, flow unimpeded at least out of the vessel having an orifice size of 5 mm (millimeters) (Klein: Seifen, Öle, Fette, Wachse 94, 12 (1968)).

"Finely divided" means a powder having a majority (>50%) of a particle size of 20 to 200 μm in diameter.

"Coarse-grained" means a product having a majority (>50%) of a particle size of 200 to 2000 μm in diameter.

The term "dust-free" means that the product only contains small fractions (<5%) of particle sizes <100 μm in diameter.

In the granulation or compacting, it is advantageous to use customary organic or inorganic aids, or carriers, such as starch, gelatin, cellulose derivatives or similar substances as are customarily used in food or feed processing as binders, gelation agents or thickeners, or of further substances, for example silicic acids, silicates (EP-A 0 743 016) stearates.

In addition, it is advantageous to provide the surface of the resultant granules with oils, as described in WO 04/054381. As oils, use can be made of mineral oils, vegetable oils or mixtures of vegetable oils. Examples of such oils are soya oil, olive oil, soya oil/lecithin mixtures. Similarly, silicone oils, polyethylene glycols or hydroxyethylcellulose are also suitable. Treating the surfaces with the said oils achieves an increased abrasion resistance of the product and a reduction of the dust fraction. The oil content in the product is 0.02 to 2.0% by weight, preferably 0.02 to 1.0% by weight, and very particularly preferably 0.2 to 1.0% by weight, based on the total amount of the feed additive.

Preference is given to products having a fraction of ≥97% by weight of a particle size of ≥100 to 1800 μm, or a fraction of ≥95% by weight of a particle size of ≥300 to 1800 μm in diameter. The fraction of dust, that is particles having a particle size <100 μm, is preferably >0 to 1% by weight, particularly preferably at most 0.5% by weight.

Alternatively, the product can also be taken up on an organic or inorganic carrier known and customary in feed processing, for example silicic acids, silicates, meals, brans, flours, starches, sugars or others and/or mixed and stabilized using customary thickeners or binders. Application examples and methods for these are described in the literature (Die Mühle+Mischfuttertechnik 132 (1995) 49, page 817).

Finally, the product can also, by means of coating methods using film-forming agents, for example metal carbonates, silicic acids, silicates, alginates, stearates, starches, gums and cellulose ethers, as described in DE-C 41 00 920, be brought into a state in which it is stable against digestion by animal stomachs, in particular the stomach of ruminants.

To set a desired amino acid concentration in the product, depending on requirements, the corresponding amino acid can be added during the method in liquid or solid form in the form of a concentrate or if appropriate a substantially pure substance or salt thereof. These can be added individually or as mixtures to the resultant or concentrated fermentation broth, or else during the drying or granulation process.

In the case of lysine, the solid product produced in this manner has, on a fermentation broth basis, a lysine content (calculated as lysine base) of 10% by weight to 70% by weight, preferably 30% by weight to 60% by weight, and very particularly preferably 40% by weight to 60% by weight, based on the total amount of the product.

In studies it has been found that setting the pH in the fermentation broth to ≤pH 5.2, increasing the sulphate/lysine ratio and optionally sulphite addition of, 0.01 to 0.5% by weight in the fermentation broth after the fermentation significantly reduces the lysine loss during the workup of the fermentation broth.

Combination of the various measures before the workup leads here to a synergistic effect compared with the sum of the individual effects.

In untreated fermentation broths (no addition of one of the additives), during the concentration to form the concentrate, an average lysine loss of approximately 3.5% results (without granulation step). Increasing the sulphate ratio by adding ammonium sulphate leads at the end to an average lysine loss of approximately 3.2%, setting the pH alone reduces the average lysine loss to approximately 1.4%.

The combination of pH setting and increasing the sulphate ratio shows a higher protective action for the lysine and results in an average lysine loss of approximately 0.9%. The combination of pH setting and sodium hydrogensulphite addition, together with the combination of all three additives, gives an average lysine loss of only approximately 0.6% or approximately 0.7%, respectively. Therefore in general, lysine loss has not be taken into account during calculating the sulfate/L-lysine ratio.

Thus it has been clearly shown that the pretreatment of lysine-containing fermentation broth by lowering the pH, increasing the sulphate balance and adding sulphite has a protective effect on the lysine present. In addition, the light colour of the product and stability under thermal stress is improved.

1. Experimental Procedures 1.1 Fermentation

Fermentations were carried out according to EP 0 533 039. The granules were produced therefrom according to the method described in EP-B 0 809 940. The granules A to D thus produced were compared with the granules E and F produced according to the invention. The L-lysine content of the samples was standardized and set to approximately 51 to 52%.

1.2 Colour Measurement

The L*a*b* colour measurement was carried out as follows:

Principle

The 3-range colorimeter for measurement of colour and reflectance operates by the principle described in DIN 5033, according to which the diffuse reflection of the sample is measured at an angle of 8°. The reflected light is transmitted into the instrument via a light guide for splitting on the exactly defined standard colour filter. Measurement is performed against a calibration standard.

Equipment:

Colorimeter Micro Color II LMC (manufacturer Dr. Lange)

Micro Color II Laboratory Station LDC 20

White standard LZM 076

Positioning cap

Light-protection cap φ 50 mm
Powder cuvette φ 34 mm
Procedure
calibrate Micro Color II (in accordance with operating instructions)
select analysis programme (→L*a*b*)
after calibration attach positioning cap
charge product into the clean cuvette up to two thirds full loosely
carefully shake product to achieve uniform filling
clean cuvette base using a soft cloth
place the cuvette on the measurement orifice and cover using the light-protection cap
measure
Note
In the measurement of pulverulent substances, care must be taken to ensure a uniform particle size (as small as possible).
With coarse-grained substances, duplicate measurement is carried out.
Explanations of the L*a*B* System:
L*: black-white range
a*: red-green range
b*: yellow-blue range
1.2.1 Colour Measurement of Products from Comparative Experiments and Products According to the Invention.

TABLE 1

|   | Lysine [%] | pH (10% in water) | [%] L* | [%] a* | [%] b* | Sulphate/ lysine ratio |
|---|---|---|---|---|---|---|
| A | 51.4 | 5.6 | 60 | 9 | 16 | 0.83 |
| B | 52.3 | 5.7 | 62 | 8 | 17 | 0.82 |
| C | 51.3 | 5.6 | 60 | 8 | 19 | 0.84 |
| D | 52.5 | 5.3 | 61 | 9 | 21 | 0.83 |
| E | 51.6 | 4.6 | 67 | 8 | 25 | 0.9 |
| F | 52.5 | 4.5 | 76.0 | 5.0 | 26.0 | 0.95 |

Table 1 lists the results of the colour determination for the comparative experiments A to D. Even without acidifying the fermentation broth, products are obtained having an acidic pH, the colour values of which, however, do not achieve those of the inventive products.
Samples E and F correspond to the inventive products which were obtained after acidifying the broth to pH 5.1, 0.2% by weight of sodium bisulphite being additionally added to the broth used to produce sample F.
It is found that samples E and F are markedly lighter than the products of the prior art. The sulphate/lysine ratio is determined from the formula $2 \times [SO_4^{2-}]/[L\text{-lysine}]$=ratio.
1.3 Product Stability after Thermal Stress
Table 2 shows the superiority of the inventive products E and F under thermal stress in relation to lower L-lysine loss.
1.4 Water Uptake (Hygroscopicity)
1.4.1 Measurement of Water Uptake (Hygroscopicity-Test)
Principle: The water uptake of powdered or granulated substances is determined by exposing them for a certain period of time to standardized climatic conditions of 40° C. and 75% re. humidity (according to ICH). The water uptake is determined gravimetricly.
Equipment: Climatic chamber standard climate 40° C./75% rel. humidity, flat weighing bottles with glass lid (5 cm in diameter), analytical balance (readability 0.0001 g)
Procedure: Determine the tare of the weighing bottle with lid
accurately weigh of 5 g of the homogeneous mixed substance into weighing bottle
the open weighing bottle is stored in the climatic chamber under the following conditions:
Temperature=4° C.
Humidity, rel.=75%
Time=1 h, 4 h
weigh closed weighing bottle after 1 h and 4 h calculate
Calculation $$\text{Water uptake } \frac{((A-T)-E) \times 100}{E} [\%]$$

A=weight after 1 h, 4 h in g
T=tare of the weighing bottle with lid in g
E=weight substance in g
Note: To determine the course of the water uptake weigh every hour during the first 6 hours of the test and after 24 h.
Diagram:
x-axis: time in h
y-axis: water uptake
1.4.2 Water Absorption of Products from Comparative Experiments and Products According to the Invention
FIG. 1 shows that the inventive product E absorbs lower amounts of water/time than the products A to D according to the prior art.
A lower hydroscopicity is of great importance for processability.

TABLE 2

Stability under thermal stress (85° C.).

|  |  | A Lys (%) | B Lys (%) | D Lys (%) | E Lys (%) | F Lys (%) |
|---|---|---|---|---|---|---|
| 85° C. | Initial | 51.4 | 52.3 | 52.5 | 51.6 | 52.2 |
|  | 1 week | 48.4 | 49.4 | 49.1 | 50.8 | 52.0 |
|  | 2 weeks | 48.5 | 48.1 | 47.1 | 50.3 | 51.2 |
|  | 3 weeks | 48.2 | 46.8 | 47.3 | 49.8 | 51.1 |
|  | diff. % abs | −3.2 | −5.5 | −5.2 | −1.8 | −1.4 |

1. Production Experiments
The fermentations were carried out according to EP-B 0 533 039.
Granulation was carried out according to EP-B 0 809 940 (U.S. Pat. No. 5,840,358).
2.1 Comparative Experiment, Prior Art
Fermentation was carried out as described in EP 0 533 039 and no biomass was separated off. The following values are obtained (L-lysine content is calculated as content of lysine base in the dry mass):

TABLE 3

| L-Lysine content (% by weight) (without water) | pH | Sulphate/lysine ratio |
|---|---|---|
| 57.2 | 7.8 | 0.82 |

100 kg of the fermentation broth were heated to 65° C., transferred to an evaporator and concentrated there at 82° C. and −0.5 bar vacuum.
The concentrated broth was granulated according to EP-B 0 809 940.

This gave an L-lysine loss of 5.1%.

TABLE 4

| L-Lysine content (% by weight) (without water) | Water (%) |
|---|---|
| 52.1 | 2 |

2.2 Addition of Ammonium Sulphate and Sulphuric Acid
The specification of the fermentation broth was as follows:

TABLE 5

| L-Lysine content (% by weight) (without water) | pH | Sulphate/lysine ratio |
|---|---|---|
| 57.7 | 7.5 | 0.9 |

1.35 kg of ammonium sulphate solution (37% solids fraction) were added to 100 kg of the fermentation broth so that the sulphate/lysine ratio was increased to 0.93.

The pH was lowered to pH 5.2 by adding 0.54 kg of sulphuric acid (approximately 93% strength), so that the initial L-lysine content decreases from 57.7% to 55.7%.

TABLE 6

| L-Lysine content (% by weight) (without water) | pH | Sulphate/lysine ratio |
|---|---|---|
| 55.7 | 5.2 | 0.93 |

The resultant fermentation broth was heated to 55° C. and then concentrated and granulated as in example 2.1.

This gave a loss of 3.3% and thus an improvement of approximately 35% compared with the comparative experiment.

TABLE 7

| L-Lysine content (% by weight) (without water) | Water (%) |
|---|---|
| 52.4 | 2.55 |

2.3 Addition of Ammonium Sulphate, Sulphuric Acid and Sodium Hydrogensulphite
The specification of the fermentation broth used was as follows:

TABLE 8

| L-Lysine content (% by weight) (without water) | pH | Sulphate/lysine ratio |
|---|---|---|
| 57.3 | 7.8 | 0.95 |

The sulphate/L-lysine ratio after fermentation amounted to 0.95, so that no further ammonium sulphate was added.

0.105 kg of sodium hydrogensulphite was added to 100 kg of the fermentation broth, stirred for 30 min and subsequently 0.61 kg of sulphuric acid was added, a pH of 5.2 being established.

Adding the hydrogensulphite lowers the L-lysine content to 57.0%, and the acid addition lowers it further to 55.1% owing to the dilution effect, the amount of dry mass increases.
The specification of the fermentation broth was as follows:

TABLE 9

| L-Lysine content (% by weight) (without water) | pH | Sulphate/lysine ratio |
|---|---|---|
| 55.1 | 5.2 | 0.96 |

The resultant fermentation broth was heated to 55° C. and then concentrated and granulated as in example 2.1.

TABLE 10

| L-Lysine content (% by weight) (without water) | Water (%) |
|---|---|
| 53.0 | 1.9 |

This gave an L-lysine loss of 2.1% and thus an improvement by virtually 60% compared with the comparative experiment.

The invention claimed is:

1. Method for producing a granulated L-lysine-containing feed additive comprising
    a) fermenting L-lysine-producing microorganism in an aqueous medium under aerobic conditions to form a fermentation broth containing biomass and L-lysine, thereby completing the fermentation,
    b) determining, when desired, sulphate/L-lysine ratio (V) in the fermentation broth, where $V=2\times[SO_4^{2-}]/[L\text{-lysine}]$,
    c) lowering pH by adding sulphuric acid to 4.9 to 5.2,
    d) setting the sulphate/L-lysine ratio to 0.85 to 1.2 by adding ammonium sulphate or sulphuric acid, if necessary, and
    e) granulating the mixture resulting from steps c) and d) to form a product, which granular product has an L-lysine content of 10 to 70% by weight (determined as lysine base, based on the total amount) and a pH of 3.5 to 5.1, measured as a suspension of 10% strength.

2. Method according to claim 1, in which the broth is concentrated by removal of water between steps c) and d).

3. Method according to claim 1, in which, before step e) adding ammonium-, earthalkali- or an alkali metal hydrogensulphite or mixtures thereof in an amount of 0.01 to 0.5% by weight, based on fermentation broth.

4. Method according to claim 1, in which, after completion of step a) partially or completely removing the biomass formed during the fermentation.

5. Method according to claim 1, in which the surface of the granular product is coated with an oil in an amount of 0.02 to 2% by weight, based on the total amount of the feed additive.

6. Method according to claim 1, wherein the L-lysine-producing microorganism is coryneform bacteria.

7. Method according to claim 1, wherein the L-lysine-producing microorganism is corynebacteria.

8. Method according to claim 1, where ammonium sulphate present in the fermentation broth after the completion of step a) meets the sulphate/L-lysine ratio.

* * * * *